United States Patent [19]

Good et al.

[11] Patent Number: 5,250,299
[45] Date of Patent: Oct. 5, 1993

[54] SYNERGISTIC ANTIMICROBIAL COMPOSITIONS

[75] Inventors: Stephen R. Good, Elkhart, Ind.; Graham S. Byng, Woodenville, Wash.

[73] Assignee: Haarmann & Reimer Corp., Springfield, N.J.

[21] Appl. No.: 763,899

[22] Filed: Sep. 23, 1991

[51] Int. Cl.$^5$ .............................................. A61K 37/50
[52] U.S. Cl. .................................. 424/94.4; 426/335; 426/56
[58] Field of Search .................. 424/94.4; 426/335, 56

[56] References Cited

U.S. PATENT DOCUMENTS 4,320,116  3/1982  Bjorek .................................. 424/610
5,043,176  8/1991  Bycroft et al. ...................... 426/332

FOREIGN PATENT DOCUMENTS 0252051  1/1988  European Pat. Off. .
0307376  11/1989  European Pat. Off. .
WO02600  4/1988  PCT Int'l Appl. .

Primary Examiner—Douglas W. Robinson
Assistant Examiner—Jean C. Witz
Attorney, Agent, or Firm—M. G. Boguslaski

[57] ABSTRACT

The invention discloses an antimicrobial composition composed of a hypothiocyanate generating system adjusted to a pH between about 1.5 and about 5 with a di or tricarboxylic acid. This composition provides synergistically improved antimicrobial action. With the addition of the organic acid, the antimicrobial composition provides effective cidal activity against Gram negative microorganisms in 20 minutes or less. The composition is particularly effective against Salmonella and may be used to provide greater than 6 logs reduction in viable cell count.

15 Claims, No Drawings

SYNERGISTIC ANTIMICROBIAL COMPOSITIONS

FIELD OF THE INVENTION

The invention relates to antimicrobial compositions in general, and, more particularly, to synergistic combinations of a hypothiocyanate generating system and a dicarboxylic or tricarboxylic acid in particular. Preferred combinations include a hypothiocyanate generating system composed of peroxidase, thiocyanate and peroxide and a carboxylic acid such as citric, fumaric, or malic acid.

BACKGROUND OF THE INVENTION

The lactoperoxidase system (LPS) is a well known antimicrobial system and is composed of lactoperoxidase, thiocyanate and hydrogen peroxide. The system occurs naturally in milk. Although the mechanism of action is not completely understood, it is postulated that the system catalyses the oxidation of thiocyanate to hypothiocyanate and that the active antimicrobial is hypothiocyanate. Although LPS is known to affect Gram negative organisms such as Salmonella, the effect has been shown to require 3 to 4 hours of contact.

European Patent Application, publication no. 0 252 051, assigned to EWOS aktieboieg, discloses that the addition of an acid to adjust the pH of the lactoperoxidase enzyme in the dry state to between 3.25 and 6, increases the storage stability of the enzyme. Acids such as hydrochloric acid, sulphuric acid, nitric acid, citric acid, acetic acid, formic acid and others as well as acidifying buffering systems as citric acid-citrate buffering systems, phosphoric acid-phosphate buffer systems, and others are suggested.

In PCT application, international publication no. WO 88/02600, Poulsen discloses a bactericidal composition composed of lactoperoxidase, thiocyanate and peroxide used for dental and wound treatment preparations. U.S. Pat. No. 4,320,116, assigned to Astra-Ewos AD, discloses a process for preparing foodstuffs; using such foodstuffs to treat bacterial infections in mammals; and pharmaceutical preparations containing an antibacterial system comprising a thiocyanate, a solid, water-soluble peroxide donor and lactoperoxidase. No mention is made in either specification of pH control or adjustment.

EP application, publication number 0 307 376, assigned to EWOS Aktiebolag, discloses a composition having a microbiocide effect and comprising iodine and lactoperoxidase, a peroxide donor and a pH adjusting agent in such an amount that the pH is 3.25-7.0 when lactoperoxidase is used and the pH is between 3.5 and 6, preferably 4.5-6.5, when horse radish peroxidase is used. The term pH adjusting agent is defined as, primarily, suitable buffer systems such as citric acid-citrate buffer, phosphoric acid-phosphate buffer and other suitable buffer systems which lock the pH within appropriate range.

U.S. Pat. No. 5,043,176, commonly assigned herein, discloses that an antimicrobial polypeptide such as nisin, a hypothiocyanate generating system and a buffering component capable of providing a pH between about 3 and about 5 provide a synergistic antimicrobial combination against Gram negative bacteria.

The synergistic antimicrobial composition of this invention has been found to be an effective cidal agent against the Gram negative organisms, such as Salmonella, in a much shorter time period than the lactoperoxidase system alone. As such it will be useful to eliminate surface contaminations of food products and as a disinfectant for food processing plants.

SUMMARY OF THE INVENTION

The invention described herein provides an antimicrobial composition composed of a hypothiocyanate generating system acidified to a pH between about 1.5 and about 5 with a dicarboxylic or tricarboxylic acid. Preferred acids are chosen from the group consisting of citric acid, citramalic acid, fumaric acid, glutamic acid, isoascorbic acid, malic acid, oxalic acid, sorbic acid, succinic acid, tartaric acid and tricarballylic acid. Most preferred are citric, citramalic, fumaric and sorbic acids.

Synergistic activity is seen against Gram negative organisms when the composition is applied at about 35 degrees Centigrade or above. A preferred hypothiocyanate generating system is lactoperoxidase, thiocyanate and a peroxide. Also provided are methods of use and a method of producing the antimicrobial composition. The composition is particularly useful on surfaces associated with food processing, and on the surfaces of fresh produce and meat such as poultry.

DESCRIPTION OF THE INVENTION

The synergistic antimicrobial composition of the invention is composed of an effective amount of a hypothiocyanate generating system, with improved activity obtained by adding an effective amount of a dicarboxylic or tricarboxylic acid to provide a pH between about 1.5 and about 5. It has been found that a preferred composition (lactoperoxidase, thiocyanate and hydrogen peroxide, acidified with citric acid to a pH from about 2 to about 4) is capable of decreasing the viable count of *Salmonella typhimurium* by greater than six logs in twenty minutes.

Testing used indicated cidal activity (bacterial killing) rather than static activity. The concentration of acid in the antimicrobial composition, when used alone, had no cidal effect in the same amount of time under the same conditions and the lactoperoxidase system alone provided a viable count reduction of only one log in the same amount of time, under the same conditions. Compositions of this invention were deemed to be "synergistic" when the effect of the composition in about the same time and under the same conditions was greater that the additive effect of the components alone.

Although the lactoperoxidase system has been reported to have an inhibitory effect on Gram negative bacteria; the effect seen with the addition of an organic dicarboxylic or tricarboxylic acid is dramatically greater in a much shorter time. The system of the present invention may be used against undesirable microorganisms in general but is particularly directed to killing food borne pathogens and food spoilage organisms. Included within these classes are *Listeria monocytogenes, Salmonella typhimurium, Salmonella enteritidis, Shigella dysenteriae, Pseudomonas aeruginosa, Vibrio Cholera, Klebsiella pneumoniae* and *E. coli.*

Composition

As used herein the phrase "hypothiocyanate component" is considered equivalent to hypothiocyanate or a hypothiocyanate generating system. The hypothiocyanate component is defined herein as any composition which is capable of generating the antimicrobially active component of the lactoperoxidase system. This component is commonly believed to be hypothiocyanate. One system capable of generating hypothiocyanate is composed of peroxidase, thiocyanate and a peroxide. The phrase "lactoperoxidase system", as used herein, refers to a combination of lactoperoxidase, hydrogen peroxide and thiocyanate and is abbreviated as LPS in the tables.

The hypothiocyanate component may include any peroxidase provided that it is capable of catalysing the reaction between the peroxide and thiocyanate. For example horseradish peroxidase, lactoperoxidase or chloroperoxidase may be used. Lactoperoxidase is available commercially from Sigma Chemical Company and is the peroxidase of choice for food systems of interest because of its natural occurrence in milk.

Any thiocyanate salt may be used although natural, common alkali metal salts such as sodium and potassium thiocyanates are preferred. Sodium thiocyanate may also be obtained from Sigma.

The term "peroxide" commonly refers to hydrogen peroxide although other peroxides with the same activity may be used. A peroxide generating system may also be used. Peroxide generating systems such as a combination of glucose and glucose oxidase are well known in the art. Although hydrogen peroxide is well known to have some antimicrobial activity, and is commonly sold in drugstores in a 3% (volume/volume) strength, the concentration of hydrogen peroxide needed to act with peroxidase and thiocyanate to produce antimicrobial activity is about 1/10,000 of that concentration.

Organic acids

Dicarboxylic and tricarboxylic acids or mixtures of such acids provide better antimicrobial activity than monocarboxylic acids. With a dicarboxylic or tricarboxylic acid chosen from the group consisting of citric, citramalic, fumaric, glutamic, isoascorbic, itaconic, malic, oxalic, propionic, sorbic, succinic, tartaric or tricarballylic acids, the kill rate of the lactoperoxidase system can be increased to 4 logs or greater in 10 to 20 minutes. Preferred acids are citric, citramalic, fumaric, glutamic, isoascorbic, malic, sorbic, succinic, tartaric and tricarballylic acid. Data showing the effectiveness of these acids when added to the lactoperoxidase system against *Salmonella typhimurium* are shown in Example 4.

Preferred are citric, citramalic, fumaric and sorbic acids.

Concentration of components

Although the concentration of the components of the antimicrobial composition described herein will vary depending on the application (i.e. food use, surface application, surface disinfection), the following will serve as a guide to useful concentration ranges and their relation.

The concentration range of the acid component will be from about 0.2 % to about 0.9%. A preferred range is from about 0.2% to about 0.4%. A particularly preferred concentration is about 0.2%.

The concentration of the hypothiocyanate component generated is generally defined by the concentration of the thiocyanate salt and peroxide. Too high a concentration of peroxide may be deleterious to some foods, although if hypothiocyanate is to be generated over a period of time, after the initial concentration of peroxide is used up, addition of more peroxide may be desirable. For single use, concentrations of peroxide are between about 0.2 mM and about 3.0 mM, preferably about 0.5 mM. The thiocyanate salt will range from about 0.5 mM to about 3.0 mM, preferably about 1.5 mM.

Method of preparation

The composition is prepared by mixing the ingredients and adjusting the pH. An additional effect may be achieved by warming the pH adjusted mixture to at least about 35 degrees Centigrade. Adjusting the pH and warming the mixture may be done in any order or by adjusting the pH and warming solutions of the individual components prior to mixing.

A synergistic increase in effectiveness of the ingredients of the antimicrobial composition is seen between a pH of about 2 and a pH of about 4. Most of the work disclosed herein was done at a pH of 3.6 in order to provide consistent results for comparison.

In order to provide the most effective antimicrobial system for short term effectiveness, the mixture should be mixed and warmed to a temperature of about 37 C prior to use. This is a particularly advantageous temperature for application to freshly slaughtered poultry because the composition is brought to a temperature similar to that of the poultry and therefore the application of the composition will not close the pores on the poultry skin which closing may effectively protect undesirable bacteria from contact with the antimicrobial composition.

The antimicrobial composition is most preferably warmed to a temperature of about 37 C and held there for approximately five minutes prior to contact with a contaminated surface. Although the mechanism of action of the lactoperoxidase system in combination with a dicarboxylic or tricarboxyllic acid is not known, it is speculated that this time and temperature provide a period for the generation of the active antimicrobial component of the lactoperoxidase system. This active component may be hypothiocyanate. However, this mechanism of action is not relied upon and not required for effectiveness of the composition.

In use, the concentrations of the components may be varied to achieve the desired effect in the desired time frame. However, it was found that with the composition adjusted to a pH of about 3.6 with citric/citrate buffer and with an incubation time of about 5 minutes prior to contact with the organisms; there was a decrease of six logs in viable count of *S. typhimurium* in twenty minutes (1 million fold).

A synergistic antimicrobial solution may be generated at the site of use by passing a solution of thiocyanate and peroxide over immobilized peroxidase to produce hypothiocyanate and combining the hypothiocyanate generated with the buffering system to produce an antimicrobial solution. The pH of the antimicrobial solution may be adjusted and warmed to at least about 35 degrees centigrade prior to application or the individual components may be pH adjusted and warmed.

Application

The composition may be used as a disinfectant for cleaning surfaces and cooking utensils in food processing plants and any area in which food is prepared or served such as hospitals, nursing homes, restaurants, especially fast food restaurants, delicatessens and the like. It may also be used as an antimicrobial in food products and would be particularly useful as a surface antimicrobial on cheeses, fresh produce such as fruits and vegetables and foods on salad bars and in delis. The composition may be applied by contacting the surfaces of the food by spraying, dipping or the like. For surface application, the composition is preferably in contact with the surface for at least about 10 minutes, preferably between about 10 and 20 minutes. It is also expected that the composition will be mixed with food.

One application of particular interest is the decontamination of freshly slaughtered poultry. It is well known that poultry carry Salmonella in their feces and on their skins to the slaughter house. It is particularly important to eradicate this contaminant early in processing. The freshly slaughtered poultry in the processing line may be sprayed or emersed into a solution of the antimicrobial composition prior to the poultry being emersed in the chill tank. Because of the short time to produce effective bactericidal action, the time of the processing line need not be increased. Ten to twenty minutes of contact with the poultry surfaces prior to emersion in the chill tank would be sufficient to kill contaminating Salmonella. The thiocyanate, acid and hydrogen peroxide would then be passed over the immobilized peroxidase providing the five minute incubation period to produce the active antimicrobial. The resultant antimicrobial solution would be sprayed on the poultry as the carcasses move continuously through processing. Either or both solutions could be adjusted to a pH of between about 2 and 4.

The following examples disclose preferred embodiments of the invention, but do not limit the applicability of the invention which is solely defined by the claims.

EXAMPLES

Growth Conditions

*Salmonella typhimurium* (ATCC 14028) was maintained on an agar medium containing tryptic soy agar (Difco Labs). Stock agar slants were stored at 4° C. An overnight culture of *S. typhimurium* was prepared by inoculating a 250 mL flask containing 10 mL nutrient broth with 1 loop of culture from the stock slant and incubating at 37° C. with slow shaking at 25 rpm on a New Brunswick G24 shaker. The overnight grown culture was then used to inoculate fresh nutrient broth (1:20 inoculation level) in a 250 mL side arm flask. This flask was then incubated at 37° C., and agitated at 25 rpm until the culture reached a density of 100 units as measured using a Klett-Sommerson photometer. This density corresponded to a viable cell count of approximately $3 \times 10^8$ cells per mL. All testing was done on cells at log phase growth unless otherwise indicated.

Hypothiocyanate Generating System

A hypothiocyanate generating system consisting of sodium thiocyanate, hydrogen peroxide and lactoperoxidase (referred to herein as the lactoperoxidase system and abbreviated in the tables as LPS) was prepared by addition of the ingredients in the following order:

| | |
|---|---|
| Sodium thiocyanate | 1.5 mM |
| Hydrogen peroxide | 0.5 mM |
| Lactoperoxidase | 0.24 units/mL | was added to 9 mL of 0.2% (w/v) $KH_2PO_4$ in deionized water adjusted to pH 3.6 with hydrochloric acid (all concentrations are given for a final concentration in 10 mL of reaction mixture). Although this order of mixing appears to give the best results, it is not required to produce a synergistic antimicrobial solution. Lactoperoxidase was obtained from Sigma Chemical Co., #L-2130.

A Lactoperoxidase system-citric acid system was prepared by first adding citric acid monohydrate (Baker Chemical Co.) at a concentration of 9.5 mM (adjusted to a pH of 3.6 with NaOH or HCl) followed by the rest of the ingredients of the lactoperoxidase system as described previously.

EXAMPLE ONE

The system was incubated for 5 minutes at 37° C. with gentle agitation (25 rpm) followed by inoculation with 1 mL of the culture of *S. typhimurium*, obtained as described previously, containing $10^8$ cells per milliliter. Incubation was continued at 37° C. and samples were withdrawn at 10 and 20 minute intervals. Serial dilutions were carried out in nutrient broth and viable counts were obtained following growth of samples on nutrient broth plates with incubation at 37° C. for 48 hours.

Results:

| Test System | $Log_{10}$ Reduction in Viable Count | |
|---|---|---|
| | 10 min | 20 min LP |
| LP system (pH 3.6) | 0 | 1 |
| 9.5 mM citric acid (pH 3.6) without LP system | 0 | 0 |
| LP system plus 9.5 mM citric acid (pH 3.6) | 1 | >6 |

EXAMPLE TWO

Replace nutrient broth with deionized water.

Results:

| Test System | Log 10 Reduction in Viable Count | |
|---|---|---|
| | 10 min | 20 min |
| LP system (pH 3.6) | 0 | 1 |
| 9.5 mM citric acid (pH 3.6, without LP system) | 0 | 0 |
| LP system plus 9.5 mM citric acid (pH 3.6) | 2 | >6 |

EXAMPLE THREE

The effect varying pH.

Results:

| | Log Reduction in Viable Count After 20 minutes Incubation | | |
|---|---|---|---|
| pH | LPS + 9.5 mM Citric Acid | 9.5 mM Citric Acid no LPS | LPS Alone |
| 4.6 | 0 | 0 | 0 |
| 4.0 | 2 | 0 | 0 |
| 3.6 | >6 | 0 | 0 |
| 3.0 | >6 | 0 | 0 |
| 2.4 | >6 | 1.1 | 3 |

EXAMPLE FOUR

The effect of varying acidifying agent.

Results:

| | Log 10 Reduction in Viable Count | | | |
|---|---|---|---|---|
| | Plus LP System | | Minus LP System | |
| Acid Tested | 10 min. | 20 min. | 10 min. | 20 min. |
| Acetic | 0 | 0 | 0 | 0 |
| Ascorbic | 0 | 2 | 0 | 0 |
| Aspartic | 0 | 3 | 0 | 0 |
| Citramalic | 2 | >6 | 0 | 0 |
| Fumaric | 4 | >6 | 0 | 0 |
| Glutamic | 0 | 5 | 0 | 0 |
| Isoascorbic | 4 | 6 | 0 | 4 |
| Itaconic | 0 | 4 | 0 | 0 |
| Lactic | 0 | 2 | 0 | 0 |
| Malic | 2 | 6 | 0 | 0 |
| Nitrilotriacetic | 0 | 1 | 0 | 0 |
| Oxalic | 2 | 6 | 0 | 0 |
| Phosphoric | 0 | 1 | 0 | 0 |
| Polygalacturonic | 0 | 2 | 0 | 0 |
| Propionic | 0 | 4 | 0 | 0 |
| Sorbic | 4 | >6 | 0 | 0 |
| Succinic | 0 | 5 | 0 | 0 |
| Tartaric | 0 | 5 | 0 | 0 |
| Tricarballylic | 0 | 6 | 0 | 0 |
| LP system alone | 0 | 0 | — | — |

EXAMPLE FIVE

The effect of replacing nutrient broth with synthetic tap water.

Experiments were carried out as in Example 1 except that the original 9 mL of nutrient broth was replaced with synthetic tap water (abbreviated herein as STW). STW was made with deionized water and contained the following salts at the concentrations noted $CaCl_2$ (Baker Chemical) 0.0676 g/L; $MgCl_2 \cdot H_2O$ (Baker) 0.14 g/L; $NaHCO_3$ (Mallinckrodt) 0.21 g/L.

Log phase cells were obtained from Klett flasks at 100 units as in Example 1. Stationary phase cells were obtained from the overnight cultures at 18 to 20 hours. All flasks were sampled at 10, 20 and 30 minutes.

The results shown on the following page indicate that standard tap water may be used and that the treatment is viabile for different organisms at different stages of growth. These results indicate the commercial viability of the method.

| | | | | Log Reduction | | | | | | | | |
|---|---|---|---|---|---|---|---|---|---|---|---|---|
| | | | Initial | LPS + Cit | | | LPS alone | | | 9.5 mM Cit | | |
| Organism | Growth Phase | pH | CFU's | 10 | 20 | 30 | 10 | 20 | 30 | 10 | 20 | 30 |
| *Salmonella typhimurium* | log | 3.6 | $10^7$ | 1 | 4 | >6 | 0 | 0 | 0 | 0 | 0 | 0 |
| ATCC 14028 | | 2.8 | | >6 | >6 | >6 | 0 | 1 | 4 | 0 | 0 | 0 |
| | stat | 3.6 | $10^8$ | 0 | 1 | 4 | 0 | 0 | 0 | 0 | 0 | 0 |
| | | 2.8 | | 3 | 4 | >7 | 0 | 0 | 0 | 2 | 5 | 5 |
| *Salmonella enteritidis* | log | 3.6 | $10^7$ | 6 | >6 | >6 | 0 | 0 | 0 | 0 | 0 | 0 |
| ATCC 13076 | | 2.8 | | >6 | >6 | >6 | 3 | >6 | >6 | 0 | 0 | 0 |
| | stat | 3.6 | $10^8$ | 4 | >7 | >7 | 0 | 0 | 3 | 0 | 0 | 0 |
| | | 2.8 | | >7 | >7 | >7 | 0 | 3 | >7 | 0 | 1 | 1 |
| *Staphylococcus aureus* | log | 3.6 | $10^7$ | 0 | 0 | 1 | 0 | 0 | 0 | 0 | 0 | 0 |
| ATCC 6538 | | 2.8 | | 0 | 0 | 2 | 0 | 0 | 2 | 0 | 0 | 0 |
| | stat | 3.6 | $10^8$ | 0 | 0 | 1 | 0 | 0 | 0 | 0 | 0 | 0 |
| | | 2.8 | | 0 | 0 | 2-3 | 0 | 0 | 0 | 0 | 0 | 0 |
| *Escherichia coli* | log | 3.6 | $10^8$ | 2 | 5 | >7 | 0 | 0 | 1 | 0 | 0 | 3 |
| ATCC 8739 | | 2.8 | | 4 | >7 | >7 | 0 | 2 | 5 | 0 | 1 | 1 |
| | stat | 3.6 | $10^9$ | 0 | 0 | 1 | 0 | 0 | 0 | 0 | 0 | 0 |
| | | 2.8 | | 0 | 2 | 5 | 0 | 0 | 0 | 0 | 0 | 0 |
| *Listeria monocytogenes* | log | 3.6 | $10^7$ | 0 | 2 | 4 | 0 | 0 | 0 | 0 | 0 | 0 |
| Scott A | | 2.8 | | 3 | >6 | >6 | 0 | 1 | 4 | 0 | 0 | 0 |
| | stat | 3.6 | $10^8$ | 0 | 2 | 3 | 0 | 0 | 0 | 0 | 0 | 0 |
| | | 2.8 | | 6 | >7 | >7 | 0 | 3 | 5 | 0 | 0 | 0 |
| *Pseudomonas aeruginosa* | log | 3.6 | $10^7$ | >6 | >6 | >6 | 4 | >6 | >6 | 6 | >6 | >6 |
| ATCC 9027 | | 2.8 | | >6 | >6 | >6 | >6 | >6 | >6 | >6 | >6 | >6 |
| | stat | 3.6 | $10^8$ | 7 | >7 | >7 | 0 | 2 | 2 | 2 | 7 | >7 |
| | | 2.8 | | >7 | >7 | >7 | 3 | >7 | >7 | 5 | >7 | >7 |
| *Streptococcus faecalis* | log | 3.6 | $10^7$ | 0 | 0 | 0 | 0 | 0 | 0 | 0 | 0 | 0 |
| ATCC 8043 | | 2.8 | | 0 | 0 | 1-2 | 0 | 0 | 0 | 0 | 0 | 0 |
| | stat | 3.6 | $10^8$ | 0 | 0 | 0 | 0 | 0 | 0 | — | — | — |
| | | 2.8 | | 0 | 0 | 0 | 0 | 0 | 0 | — | — | — |
| *Shigella dysenteriae* | log | 3.6 | $10^7$ | >6 | >6 | >6 | 2 | 6 | >6 | 0 | 0 | 0 |
| ATCC 11456A | | 2.8 | | >6 | >6 | >6 | 4 | >6 | >6 | 0 | 0 | 0 |
| | stat | 3.6 | $10^7$ | >6 | >6 | >6 | 0 | 1 | 2 | 0 | 0 | 0 |
| | | 2.8 | | >6 | >6 | >6 | 4 | >6 | >6 | 0 | 0 | 1 |

It should be understood that many modifications and variations can be made in the proportions and components used herein without departing from the spirit and scope of the invention, which is solely defined by the claims.

What is claimed is:

1. An antimicrobial composition comprising a synergistic combination of an effective amount of a hypothiocyanate generating system adjusted to a pH of between about 1.5 to about 3.6 with a dicarboxylic or tricarboxylic acid selected from the group consisting of citric acid, citramalic acid, fumaric acid, glutamic acid, itaconic acid, malic acid, oxalic acid, succinic acid, tartaric acid and tricarballylic acid.

2. The composition of claim 1 in which the hypothiocyanate generating system is composed of a peroxidase, an alkali metal thiocyanate salt and a peroxide.

3. The composition of claim 2 in which the peroxidase is selected from the group consisting of horseradish peroxidase, lactoperoxidase and chloroperoxidase.

4. The composition of claim 2 in which the hypothiocyanate generating system is composed of lactoperoxidase, a thiocyanate and hydrogen peroxide.

5. The composition of claim 4 which is adjusted to a pH of between about 2 and about 3.6 with citric acid.

6. A method of disinfecting a surface contaminated with Gram negative microorganisms comprising applying the antimicrobial composition of claim 1 to a surface suspected of contamination with Gram negative microorganisms.

7. A method of disinfecting a surface associated with the preparation of foods, comprising applying the antimicrobial composition of claim 4 to such surface.

8. A method of killing Gram negative microorganisms contaminating the surface of a food product comprising adding the antimicrobial composition of claim 4.

9. A method of killing Gram negative microorganisms on a surface of a food product or on a surface used in preparation of a food product, comprising the steps of:
   a. mixing a hypothiocyanate generating system with a dicarboxylic or tricarboxylic acid selected from the group consisting of citric acid, citramalic acid, fumaric acid, glutamic acid, itaconic acid, malic acid, oxalic acid, succinic acid, tartaric acid and tricarballylic acid to produce an antimicrobial solution at a pH between about 1.5 to about 3.6; and
   b. applying to a surface of food product or a surface which contacts a food product.

10. The method of claim 9 in which the antimicrobial solution is applied by spraying.

11. A method of killing Gram negative organisms, comprising the steps of:
   a. mixing ingredients of a hypothiocyanate generating system;
   b. adjusting the mixture to a pH between about 1.5 and 3.6 with a dicarboxylic or tricarboxylic acid selected from the group consisting of citric acid, citramalic acid, fumaric acid, glutamic acid, itaconic acid, malic acid, oxalic acid, succinic acid, tartaric acid and tricarballylic acid;
   c. warming the pH adjusted mixture to a temperature of at least about 35 degrees Centigrade; and
   d. contacting the warmed mixture with a surface contaminated with a Gram negative organism for a time sufficient to kill the microorganisms.

12. A method of killing Salmonella on poultry, comprising the steps of:
   a. mixing the ingredients of a hypothiocyanate generating system;
   b. adjusting the pH of the mixture to between about 1.5 to 3.6 with a dicarboxylic or tricarboxylic acid selected from the group consisting of citric acid, citramalic acid, fumaric acid, glutamic acid, itaconic acid, malic acid, oxalic acid, succinic acid, tartaric acid and tricarballylic acid;
   c. warming the pH adjusted mixture to a temperature of at least about 35 degrees centigrade;
   d. contacting the warmed mixture with surfaces of slaughter fresh poultry; and
   e. allowing the pH adjusted mixture to remain in contact with the poultry surfaces for at least about ten minutes.

13. A method of producing a synergistic antimicrobial composition composed of a hypothiocyanate generating system adjusted to a pH of between about 1.5 and about 3.6 and dicarboxylic or tricarboxylic acid, comprising the steps of:
   a. passing a solution of thiocyanate and peroxide at over immobilized peroxidase to produce hypothiocyanate;
   b. adjusting the pH of the antimicrobial solution to a pH of between about 1.5 to about 3.6 with a dicarboxylic or tricarboxylic acid selected from the group consisting of citric acid, citramalic acid, fumaric acid, glutamic acid, itaconic acid, malic acid, oxalic acid, succinic acid, tartaric acid and tricarballylic acid;
   c. warming pH adjusted solution to a temperature of at least about 35 degrees centigrade; and
   d. contacting surfaces contaminated with Gram negative microorganisms for between 10 and 20 minutes.

14. a method of killing Gram negative organisms on fresh product, comprising applying the antimicrobial composition of claim 1 at a temperature of at least about 35 degrees centigrade to surfaces of fresh produce.

15. A method of surface disinfection, comprising contacting a surface with a solution of the antimicrobial composition of claim 1 at a temperature of at least about 35 degrees centigrade for between 10 to 60 minutes.

* * * * *